(12) United States Patent
Hedl et al.

(10) Patent No.: US 8,429,974 B2
(45) Date of Patent: Apr. 30, 2013

(54) LAMB WAVE DISPERSION COMPENSATION FOR EUSR APPROACH TO ULTRASONIC BEAM STEERING

(75) Inventors: Radek Hedl, Jedovnice (CZ); Girija Parthasarathy, Maple Grove, MN (US)

(73) Assignee: Honeywell International Inc., Morristown, NJ (US)

( * ) Notice: Subject to any disclaimer, the term of this patent is extended or adjusted under 35 U.S.C. 154(b) by 439 days.

(21) Appl. No.: 12/786,220

(22) Filed: May 24, 2010

(65) Prior Publication Data

US 2011/0058453 A1 Mar. 10, 2011

Related U.S. Application Data

(60) Provisional application No. 61/240,530, filed on Sep. 8, 2009.

(51) Int. Cl.
*G01N 29/06* (2006.01)
*G01N 29/44* (2006.01)

(52) U.S. Cl.
USPC .............. 73/602; 73/587; 73/626; 73/641

(58) Field of Classification Search ............ 73/583, 73/587, 602, 624, 625, 626, 641
See application file for complete search history.

(56) References Cited

U.S. PATENT DOCUMENTS

| | | |
|---|---|---|
| 3,674,998 A | 7/1972 | Benz |
| 4,106,327 A | 8/1978 | Adler et al. |
| 4,274,288 A | 6/1981 | Tittmann et al. |
| 4,372,163 A | 2/1983 | Tittmann et al. |
| 4,755,953 A | 7/1988 | Geithman et al. |
| 5,546,811 A | 8/1996 | Rogers et al. |
| 5,672,830 A | 9/1997 | Rogers et al. |
| 5,734,588 A | 3/1998 | Rose et al. |
| 5,956,143 A | 9/1999 | Kotidis |
| 5,992,234 A | 11/1999 | Rhodes et al. |
| 6,006,163 A | 12/1999 | Lichtenwalner et al. |
| 6,182,510 B1 | 2/2001 | Stanke et al. |
| 6,393,384 B1 | 5/2002 | Anthony et al. |
| 6,581,014 B2 | 6/2003 | Sills et al. |
| 6,996,480 B2 | 2/2006 | Giurgiutiu et al. |
| 2005/0228597 A1 | 10/2005 | Giurgiutiu et al. |
| 2008/0288184 A1 | 11/2008 | Giurgiutiu et al. |
| 2008/0289423 A1 | 11/2008 | Gordon et al. |

(Continued)

OTHER PUBLICATIONS

Victor Giurgiutiu, Lingyu Yu, and 2-Lt. Dustin Thomas, "Embedded Ultrasonic Structural Rada wtih Piezoelectric Wafer Active Sensors for Damage Detection in Cylindrical Shell Structures", Apr. 2004, American Institute of Aeronautics and Astronauts, paper # AiAA-2004-1983, pp. 114.*
Ostachowicz W., et al.; Damage Localisation in Plate-Like Structures Based on PZT Sensors; Mechanical Systems and Signal Processing, London, GB, vol. 23, No. 6, Aug. 1, 2009, pp. 1805-1829.

(Continued)

*Primary Examiner* — Peter Macchiarolo
*Assistant Examiner* — Rose M Miller
(74) *Attorney, Agent, or Firm* — Ingrassia Fisher & Lorenz, P.C.

(57) ABSTRACT

Methods and systems for detecting features in thin-wall structures are provided. A plurality of ultrasonic waves are generated within a thin-wall structure. At least one echo from the plurality of ultrasonic waves within the thin-wall structure is detected. The at least one echo is processed to determine a position of at least one feature in the thin-wall structure based on Embedded Ultrasonic Structure Radar (EUSR) beamforming performed in the frequency domain.

17 Claims, 9 Drawing Sheets

U.S. PATENT DOCUMENTS

2009/0048789 A1* 2/2009 Yu et al. ............ 702/39
2009/0067286 A1* 3/2009 Bose et al. ............ 367/38
2009/0150094 A1  6/2009 Van Velsor et al.

OTHER PUBLICATIONS

Giurgiutu V.; Chapter 7: Embedded Ultrasonic NDE With Piezoelectric Wafer Active Sensors; Advanced Ultrasonic Methods for Material and Structure Inspection, Wiley, GB, Jan. 1, 2007, pp. 237-272.

Lingyu Yu et al.; Design, Implementation, and Comparison of Guided Wave Phased Arrays Using Embedded Piezoelectric Wafer Active Sensors for Structural Health Monitoring; Smart Structures and Materials 2006: Smart Structures and Integrated Systems, Feb. 27, 2006, San Diego, CA, vol. 6173, 2006, pp. 61731M-1-61731M-12.

EP Search Report, EP 10173337.6-2204 dated Dec. 7, 2010.

* cited by examiner

LAMB WAVE DISPERSION COMPENSATION FOR EUSR APPROACH TO ULTRASONIC BEAM STEERING

CROSS REFERENCE TO RELATED APPLICATION

This application claims the benefit of U.S. Provisional Application 61/240,530, filed Sep. 8, 2009, incorporated herein by reference.

TECHNICAL FIELD

The present invention generally relates to Embedded Ultrasonic Structure Radar (EUSR), and more particularly relates to improved methods and systems for implementing EUSR beam steering/focusing.

BACKGROUND

Ultrasound technology is a widely used technique for non-destructive testing of various structures such as the hulls of vehicles and pipelines. Particularly, Lamb waves have been investigated as a type of guided ultrasound waves for investigating the structural state of plate-like, or thin-wall, structures. As is generally known, Lamb waves are elastic perturbations that propagate in a solid plate with free boundaries. During propagation through a solid plate structure, Lamb waves form several symmetric and anti-symmetric modes according to the plate thickness and acoustic frequency of the waves specified by their phase velocities. One advantage of Lamb waves is that they are able to propagate long distances in plate structures. Moreover, in contrast to conventional ultrasonic methods, where inspection of the structure is conducted point-by-point, a line is inspected at each position of a transducer. Therefore, Lamb waves may save significant time when investigating large structures.

Although ultrasound is an excellent technique for detecting structural flaws, it may be relatively inefficient when it comes to evaluating flaw size, shape, and orientation. The spatial resolution and signal to noise ratio of the resulting ultrasound image may be improved by additional numerical processing of the ultrasound data. For example, when a collection of sensors are used, the ultrasonic wave may be steered and focused to enhance the resolution and sensitivity of defect detection over an inspected region. Such methods hold great potential for implementing structural health monitoring (SHM) systems and pursuing prognostics and remaining life approaches to asset management.

Various methods for steering and focusing ultrasonic Lamb waves exist. One of these methods is known as Embedded Ultrasonic Structure Radar (EUSR). The EUSR method is one of the oldest and simplest delay-and-sum beamforming approaches. EUSR assumes that data from an N-element sensor array is collected in a "round-robin" fashion, using one sensor element at a time as a transmitter and the remaining sensor elements as receivers (either including or excluding the transmitting element). Then, with a total of N×N (or N×N−1) data signals, EUSR implements beamforming as a signal post-processing operation.

Conventionally, EUSR is performed in the time domain. As such, it does not account for the dispersion of Lamb waves. That is, conventional EUSR does not account for the dependence of ultrasonic wave velocity on the plate thickness/pulse frequency product. This dispersion results in a spatial resolution degradation of the resulting EUSR image, which decreases the accuracy (both location and size) of damage detection. One widely used approach to mitigate the impact of dispersion is to drive ultrasonic sensors using narrowband excitation pulses with center frequencies tuned to the low dispersive region for particular Lamb wave mode. However, one drawback of this approach is the limitation of pulse frequency to low dispersive part of the dispersion curve which may not be optimal for a particular application (e.g., material or defect type).

Another approach attempts to compensate for the impact of the dispersion in the input data (i.e., raw transducer data) prior to EUSR processing. Such algorithms attempt to compensate for the elongation of an ultrasonic pulse when propagating in dispersive material, thereby resulting in spatial resolution in the direction of the beam propagation. An improvement of the spatial resolution in the direction of beam propagation may be observed, though no effect in the perpendicular direction is clearly demonstrated.

Accordingly, it is desirable to provide an improved method and system for implementing ultrasound for use in the detection of structural flaws. Furthermore, other desirable features and characteristics of the present invention will become apparent from the subsequent detailed description and the appended claims, taken in conjunction with the accompanying drawings and the foregoing technical field and background.

BRIEF SUMMARY

In one embodiment, a method for detecting features in a thin-wall structure is provided. A plurality of ultrasonic waves are generated within the thin-wall structure. At least one echo from the plurality of ultrasonic waves within the thin-wall structure is detected. The at least one echo is processed to determine a position of at least one feature in the thin-wall structure based on Embedded Ultrasonic Structure Radar (EUSR) beamforming performed in the frequency domain.

In another embodiment, a method for detecting features in a thin-wall structure is provided. A plurality of ultrasonic waves are generated within the thin-wall structure with a plurality of sensors coupled to the thin-wall structure. At least one echo from the plurality of ultrasonic waves within the thin-wall structure is detected with the plurality of sensors. The at least one echo is processed to determine a position of at least one feature in the thin-wall structure based on EUSR beamforming performed in the frequency domain.

In a further embodiment, a system for detecting features in a thin-wall structure is provided. The system includes a thin-wall structure, a plurality of sensors coupled to the thin-wall structure, and a processing system in operable communication with the plurality of sensors. The processing system is configured to generate a plurality of ultrasonic waves within the thin-wall structure with the plurality of sensors coupled to the thin-wall structure, detect at least one echo from the plurality of ultrasonic waves within the thin-wall structure with the plurality of sensors, and determine a position of at least one feature in the thin-wall structure based on the detected at least one echo. The determining of the position of the at least one of the features is based on EUSR beamforming performed in the frequency domain.

BRIEF DESCRIPTION OF THE DRAWINGS

The present invention will hereinafter be described in conjunction with the following drawing figures, wherein like numerals denote like elements.

DETAILED DESCRIPTION

The following detailed description is merely exemplary in nature and is not intended to limit the invention or the application and uses of the invention. Furthermore, there is no intention to be bound by any theory presented in the preceding background or the following detailed description.

Disclosed herein is a modification of the generally know ultrasonic beam steering algorithm generally referred to as Embedded Ultrasonic Structure Radar (EUSR). EUSR transmitter beamforming is based on the principle of constructive interference in a bundle of rays emitted from an array of sensor elements at a required steering angle, and destructive interferences anywhere else. This can be simply achieved by applying an appropriate time delay to each transmitted signal with regard to individual transmitter (sensor) position. The receiver beamforming is reciprocal to the transmitter beamforming However, original EUSR does not account for dispersion of Lamb waves (i.e. dependence of ultrasonic wave velocity on plate thickness/pulse frequency product). The dispersion results in degradation of spatial resolution of resulting EUSR image, which decreases accuracy of defect localization and sizing.

Figure 1:
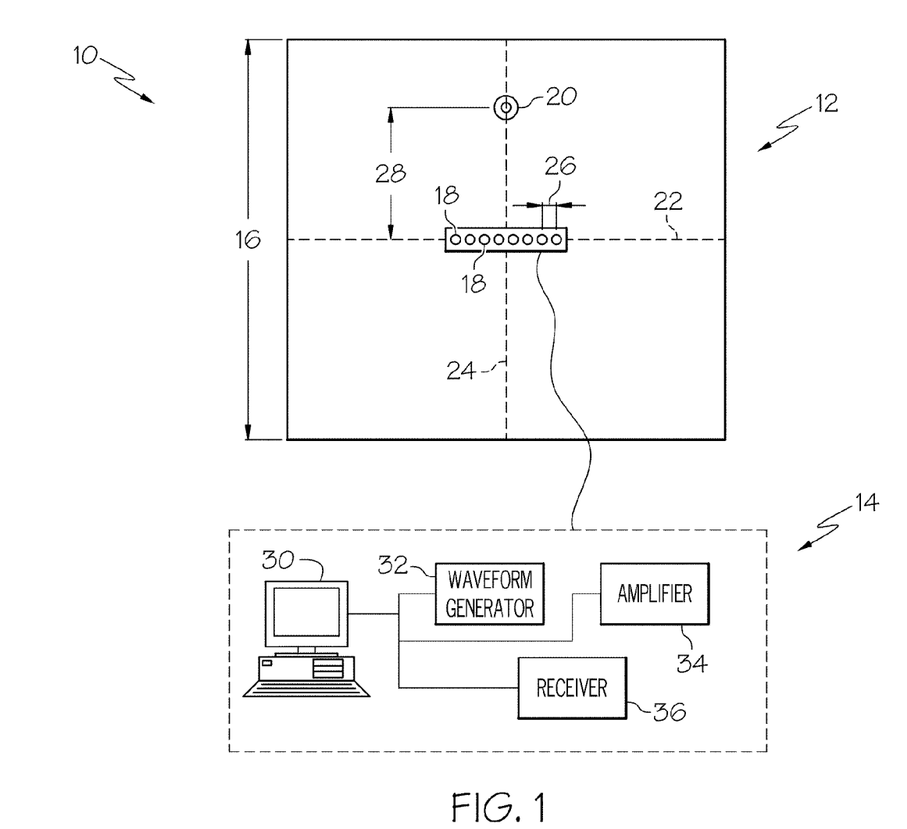
FIG. 1 is a plan schematic view a system for detecting damage in a thin-wall structure according to an embodiment.

FIG. 1 illustrates a system 10 for testing a thin-wall structure for damage according to one embodiment of the present invention. The system includes a thin-wall (or plate-like) structure 12 and a control system 14.

In the depicted embodiment, the thin-wall structure 12 is a square aluminum plate with a side length 16 of approximately 1000 mm and a thickness (not shown) of approximately 1 mm. The thin-wall structure 12 includes an array of ultrasonic transducers 18 (i.e., actuators/sensors) and a simulated damage feature 20 mounted thereto. In the depicted embodiment, there are eight ultrasonic transducers 18 linearly arranged along a first bisecting axis 22 of the thin-wall structure 12 with half being on each side of a second bisecting axis 24 of the thin-wall structure 12. Adjacent ultrasonic transducers 18 are separated by a distance 26 of approximately 5 mm. The ultrasonic transducers 18 may be piezoelectric transducers, as is commonly understood. In one embodiment, the ultrasonic transducers are Noliac CMAP06 Ceramic Multilayer Actuator Plates, having length of 3 mm, a width of 3 mm, and a thickness of 2 mm.

In the depicted embodiment, the damage feature 20 is in the form of a steel washer fixed on the surface of the thin-wall structure by means of double-sided tape (allowing the defect to be moved between experiments). The damage feature 20 is positioned a distance 28 away from the transducers 18 and/or the first axis 22 of the thin-wall structure 12. In one example, the steel washer has an outer diameter of 16 mm, an inner diameter of 6 mm, and a thickness of 1.5 mm (not shown).

The control system 14 includes control computer 30, a waveform generator 32, an amplifier 34, and a receiver 36, among other components. One or more of the components of the control system 14 includes a processor, which may be any one of numerous known general-purpose microprocessors or an application specific processor that operates in response to program instructions. The processor may include on-board random access memory (RAM) and on-board read only memory (ROM) that have program instructions stored thereon for carrying out the processes described herein. In one experiment, an Agilent 33220A 20 MHz Function/Arbitrary Waveform Generator, a Krohn-Hite KH 7500 Wideband Power Amplifier, and an Olympus 5800PR Computer controlled ultrasonic pulser/receiver were used.

In one experiment, ultrasonic waves were created within the thin-wall structure 12 with an excitation pulse including six cycles of sine pulse bursts, weighted by a Gaussian window, applied to the transducers 18. The burst period was set to 15 ms to assure that all reverberation was dismissed before the next burst was transmitted. The main frequency of the excitation pulse was tuned to 210 kHz to generate dominant A0 mode. The signal sampling frequency was 10 MHz. EUSR was then used (i.e., by the control computer 30) to process the signals (i.e., echoes) detected by the transducers 18. According to one aspect of the present invention, EUSR beamforming was performed in the frequency domain.

Generally, the EUSR method assumes that data from an N-element sensor array is collected in a "round-robin" fashion using one sensor element at a time as a transmitter and the remaining sensor elements as receivers (either including or excluding the transmitting element). Then, with a total of N×N (or N×N−1) data signals, EUSR implements beamforming as a signal post-processing operation.

EUSR transmitter beamforming is based on the principle of constructive interference in the bundle of rays emitted by an array of sensor elements at a required angle φ and destructive interferences anywhere else. This can be achieved by applying an appropriate time delay to each transmitted signal with regard to individual transmitter position. The so-called simple EUSR (S-EUSR) algorithm uses the parallel ray approximation to simplify the beamforming calculation. With the origin of the coordinate system located in the phase center of the linear sensor array, the delay for individual transmitters can be calculated using Equation (1), as follows:

$$\delta_m(\varphi, m) = m \frac{D \cos(\varphi)}{c}, \quad (1)$$

where m represents the $m^{th}$ sensor in the linear array, D is the sensor spacing, c is the ultrasonic velocity for the material of the thin-wall structure given by Lamb wave dispersion curve for particular Lamb wave mode as a function of the wave frequency—structure thickness product, and φ corresponds to the expected beam steering angle.

This simplifying parallel ray approximation is valid only if the target is relatively far away from the sensor array. When the target is not sufficiently far away from the array, wave propagation direction varies from one array element to another and individual direction vectors need to be assigned to each sensor. Therefore, for the near field region, the so-called generic EUSR (G-EUSR) approach has been developed. With this approach, the calculated signal delay depends not only on the steering angle and transmitter position, but also the target position, and may be expressed as $$\delta_m(\vec{r}, \vec{r}_m) = \frac{(r - r_m)}{c}, \quad (2)$$

where $\vec{r}$ is the position vector of the target, $\vec{r}_m = \vec{r} - \vec{s}_m$, $\vec{s}_m$ is the position vector of the $m^{-th}$ sensor, and c is the ultrasonic velocity.

Figure 2:
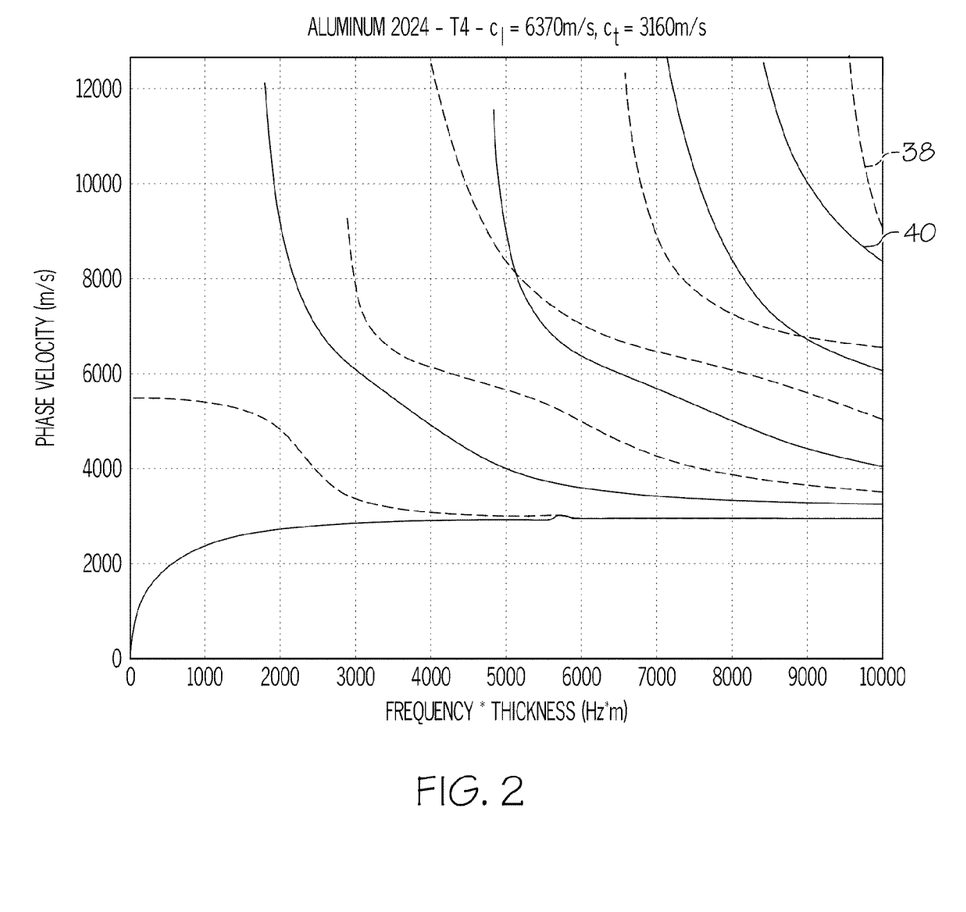
FIG. 2 is a graph depicting exemplary dispersion curves for Aluminum 2024-T4.
Figure 3:
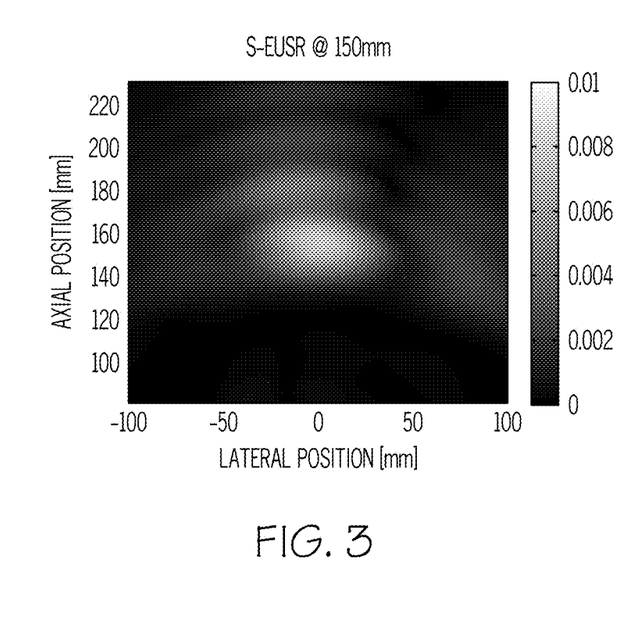
FIGS. 3-14 are images of a damage feature on a thin-wall structure, generated using conventional EUSR and the EUSR method described herein.
Figure 4:
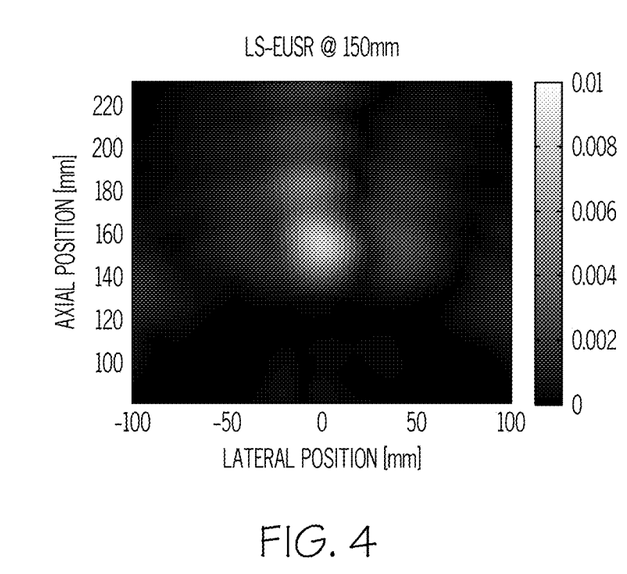
Figure 5:
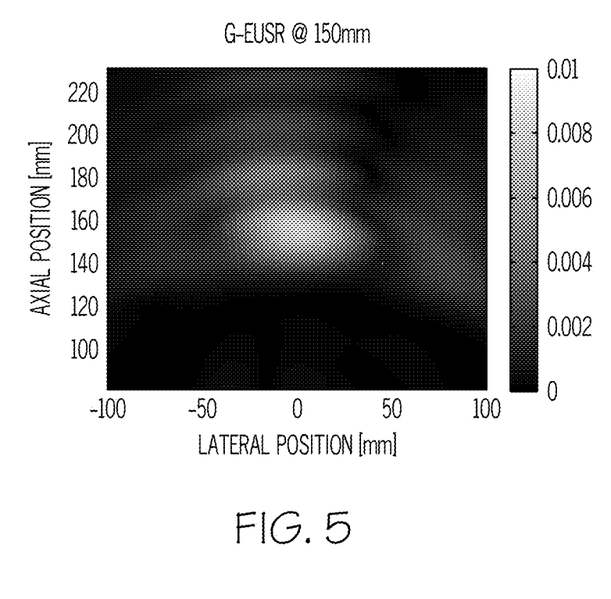
Figure 6:
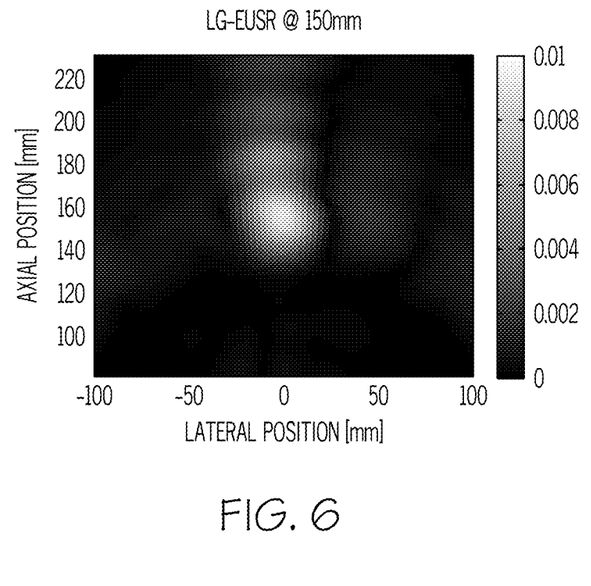
Figure 7:
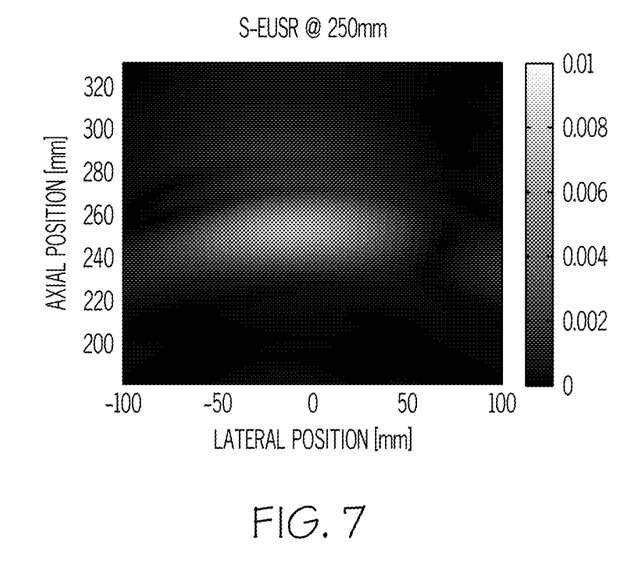
Figure 8:
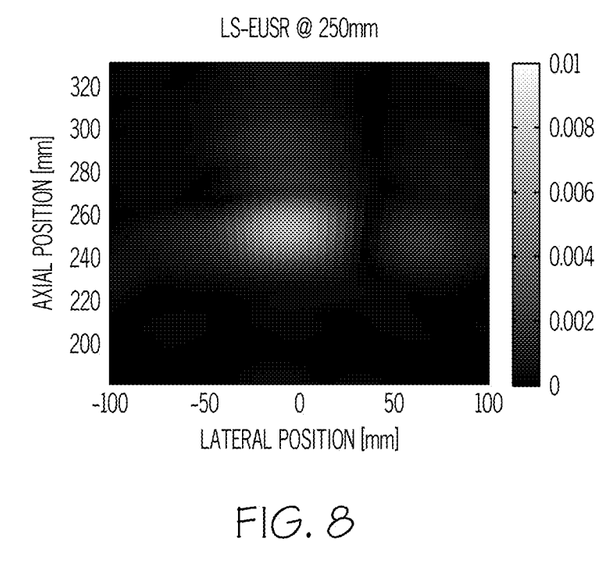
Figure 9:
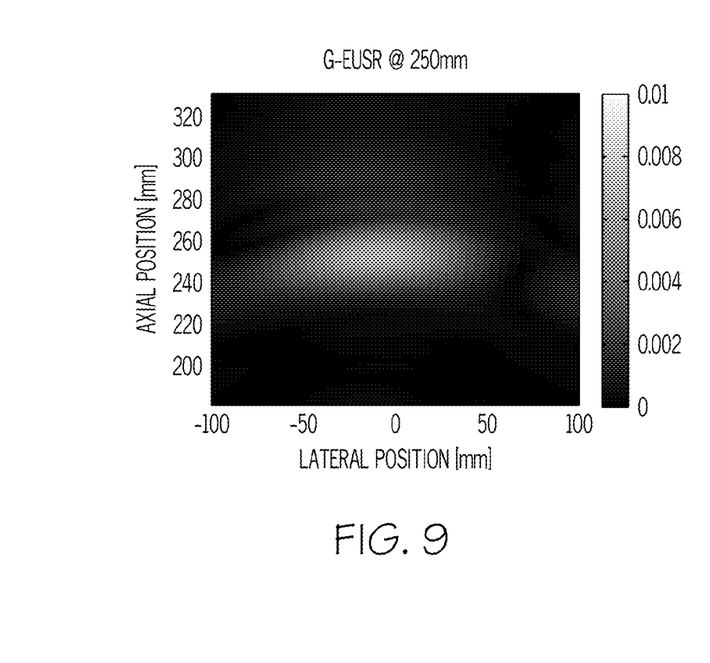
Figure 10:
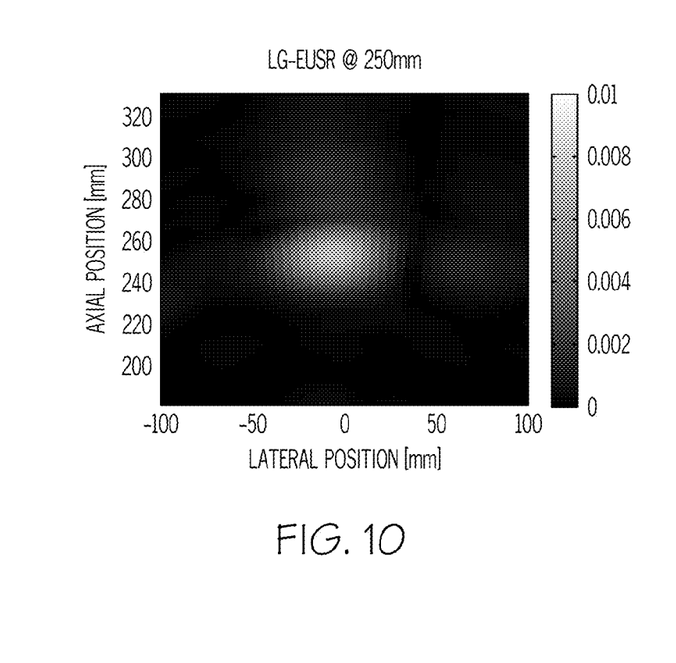
Figure 11:
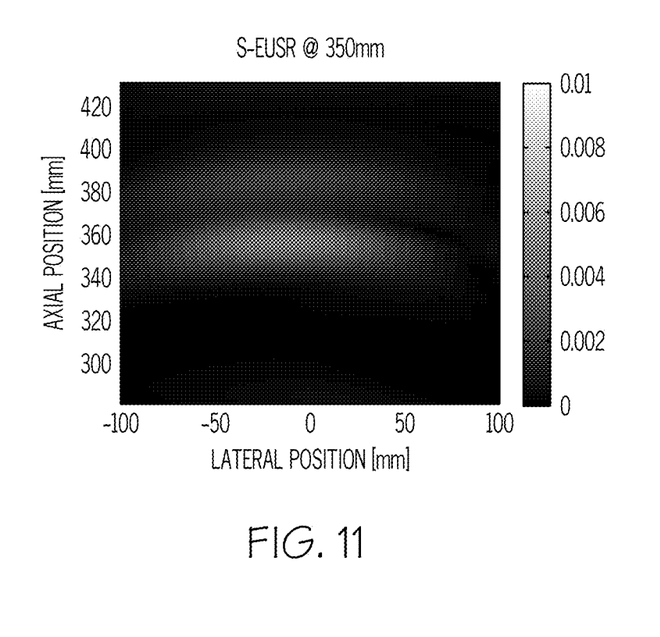
Figure 12:
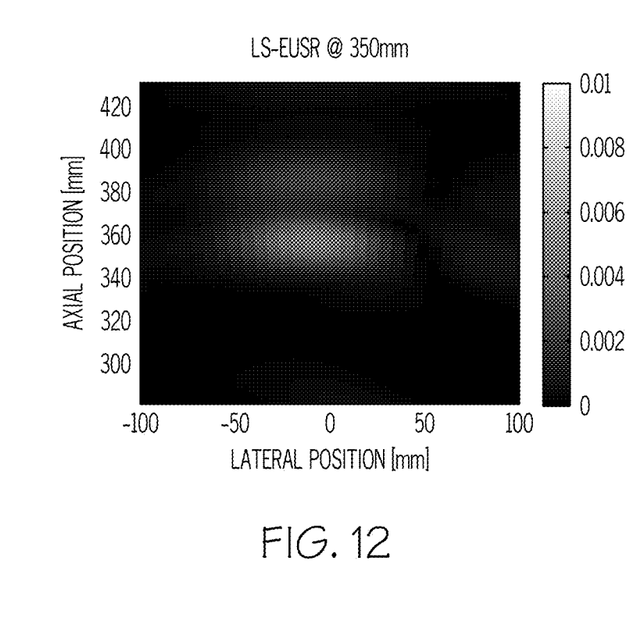
Figure 13:
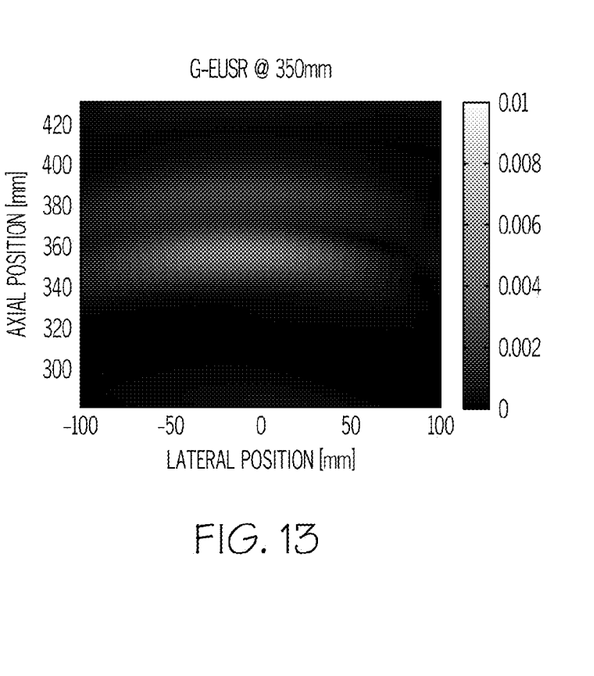
Figure 14:
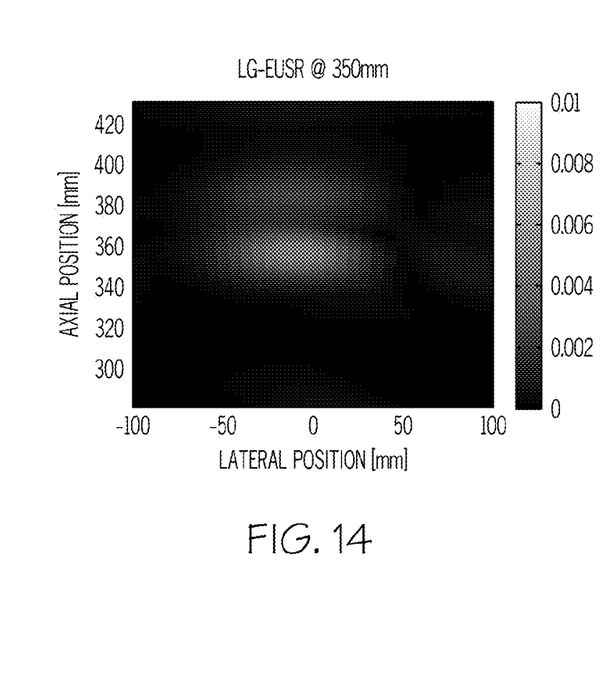

The receiver beamforming is reciprocal to the transmitter beamforming. Hence, the signals received at all of the sensors may be synchronized by delaying them by $\delta_m$ (i.e., Equation 1 for S-EUSR or Equation 2 for G-EUSR). The time delay for beamforming varies with ultrasonic wave frequency. The dependence of the wave velocity on the wave frequency is given by the Lamb wave dispersion curve for the particular wave propagation material and the particular Lamb wave mode. Exemplary dispersion curves for Aluminum 2024-T4 are depicted in FIG. 2, with the symmetric modes being shown with dashed lines 38 and asymmetric modes being shown with solid lines 40.

Conventionally, EUSR is performed in the time domain. As such, it does not account for the dispersion of Lamb waves. That is, conventional EUSR does not account for the dependence of ultrasonic wave velocity on the plate thickness/pulse frequency product. This dispersion results in a spatial resolution degradation of the resulting EUSR image, which decreases the accuracy (both location and size) of damage detection.

In accordance with the approach disclosed herein, the delay-and-sum EUSR beamforming is conducted in the frequency domain using, for example, the Fourier transform. This allows the dispersion curve for a particular Lamb wave mode to be implemented into the EUSR calculation. As a result, spatial resolution in the direction perpendicular to the propagation of the steered beam is improved. The more considerable the dispersion, the more significant the spatial resolution improvement. In contrast to presently known approaches, the dispersion compensation is not performed prior to the EUSR processing. Rather, it is an integral part of the actual EUSR processing. Any presently known dispersion compensation/removal approach may be applied to the output of the approach disclosed herein, i.e. to the individual Lamb EUSR steered beams, to achieve improvement in both directions of the spatial resolution (parallel and perpendicular to the direction of propagation of the EUSR processed ultrasonic beam).

Consider the basic equation for the EUSR algorithm. The calculated amplitude modulation scan ("A-scan") for a particular steering angle ($\phi$) is given as a sum of appropriately delayed signals registered by individual sensors in the sensor array and may be expressed $$A(\varphi, t) = \sum_{m=1}^{N} \sum_{n=1}^{N} x_{mn}(t - \delta_m - \delta_n), \quad (3)$$

where $x_{mn}(t)$ is the signal transmitted by $m^{-th}$ sensor and registered by $n^{-th}$ sensor, N is the number of sensors in the sensor array, and $\delta_m$ and $\delta_n$ are delays for transmitter and receiver beamforming calculated using Equations (1) and (2), depending on whether near-field or far-field beamforming is applied.

Of particular interest, using the Fourier transform, Equation (3) may be rewritten in frequency domain as $$A(\varphi, t) = \sum_{m=1}^{N} \sum_{n=1}^{N} ifft[X_{mn}(\omega)e^{-i\omega(\delta_m + \delta_n)}], \quad (4)$$

where $X_{mn}(\omega)$ is the Fourier transform of the registered signal $x_{mn}(t)$ and $\omega$ is the angular frequency ($\omega = 2\pi f$). Recalling that the delays $\delta_m$ and $\delta_n$ depend on the wave velocity (see Equations (1) and (2)), and accepting that the wave velocity varies with the wave frequency, Equation (4) becomes $$A(\varphi, t) = \sum_{m=1}^{N} \sum_{n=1}^{N} ifft[X_{mn}(\omega)e^{-i\omega[\delta_m(\omega \cdot d) + \delta_n(\omega \cdot d)]}], \quad (5)$$

where d is the plate thickness. Equation (5) represents an EUSR algorithm, or method, performed in the frequency domain, in accordance with one aspect of the present invention, which is used in the system 10 shown in FIG. 1.

FIGS. 3-14 illustrate the results of various EUSR processing schemes, including the EUSR method described herein. More specifically, FIGS. 3-14 are comparisons of image results for simple EUSR and generic EUSR approaches, both with and without dispersion being accounted for (i.e., in the frequency domain), for the system shown in FIG. 1. The results depicted in FIGS. 3-14 were calculated using experimental data for simulated defect represented by a steel washer (similar to that described above) fixed on the surface of the thin-wall structure by means of double-sided sticking tape located on the sensor array axis at various distances from the array. The washer has an outer diameter of 16 mm, an inner diameter of 6 mm, and a thickness of 1.5 mm. As an excitation pulse, a 6-count Gaussian windowed sine burst, centered at 210 kHz was used.

Before applying the Lamb EUSR algorithm, the recorded waveforms were pre-processed, including windowing by a Hanning window, to eliminate the impact of transients at the beginning of the signal records. Wavelet filtration was also provided to remove zero drift and to eliminate frequency leakage.

Referring to FIGS. 3-14, the defect was located 150 mm, 250 mm, and 350 mm from the first bisecting axis 22 (FIG. 1) at 90° (i.e., on the second bisecting axis 24). As indicated in FIGS. 3-14, there is little difference between the results generated by the simple EUSR (S-EUSR) and generic EUSR (G-EUSR) approaches. It is noted, however, that the generic EUSR is beneficial when the target is located in the sensor array near field. For far field, both approaches produce similar results. Nevertheless, a comparison of the EUSR scanning images where dispersion was accounted for (i.e., LS-EUSR and LG-EUSR) and EUSR scanning images where dispersion was not accounted for (i.e., S-EUSR and G-EUSR) shows significant improvement of spatial resolution in the direction perpendicular to the propagation of the EUSR steered beam.

Table I below summarizes the lateral and axial spatial resolution measured as Full-Width-at-Half-Maximum (FWHM) of a defect response, the estimated image signal/noise ratio, and the time required for processing for the various EUSR approaches. LS-EUSR and LG-EUSR beam steering approaches appear to nearly double spatial resolution in the direction perpendicular to beam propagation (i.e., lateral) over the S-EUSR or G-EUSR approaches. Generally, the ratio of the lateral spatial resolution improvement varies from case to case.

Experimentally, it has been found that the more significant the dispersion, the more considerable the spatial resolution improvement. Thus, it seems to be advantageous to drive sensors using a pulse with a center frequency tuned to a high dispersive area of the dispersion curve. It can also be seen that axial spatial resolution (i.e., parallel to the direction of the steered beam) remains unchanged. An improvement can also be observed in the signal to noise ratio in the EUSR steered images. In the case of simple EUSR the improvement was about 2 dB and for generic EUSR the improvement was approximately 3 dB.

TABLE 1

| Defect position | | S-EUSR Artificial data | LS-EUSR Real data | G-EUSR Artificial data | LG-EUSR Real data |
|---|---|---|---|---|---|
| 150 mm | Lateral spatial resolution [mm] | 60 | 30 | 60 | 32 |
| | Axial spatial resolution [mm] | 30 | 31 | 30 | 30 |
| | Signal/noise ratio [dB] | 18 | 20 | 19 | 22 |
| 250 mm | Lateral spatial resolution [mm] | 97 | 52 | 92 | 52 |
| | Axial spatial resolution [mm] | 26 | 25 | 25 | 25 |
| | Signal/noise ratio [dB] | 17 | 19 | 18 | 20 |
| 350 mm | Lateral spatial resolution [mm] | 118 | 72 | 118 | 65 |
| | Axial spatial resolution [mm] | 21 | 22 | 21 | 22 |
| | Signal/noise ratio [dB] | 14 | 16 | 14 | 17 |
| | Processing time [min] | 1.1 | 1.1 | 128.5 | 174.3 |

It should be noted that the known methods previously described result in spatial resolution improvement in the direction parallel to the propagation of the steered beam. Therefore, in at least some embodiments, it may be preferable to implement a hybrid algorithm. Such a hybrid algorithm would include: calculation of EUSR A-scans using either simple or generic Lamb EUSR, and application of the dispersion compensation/removal algorithm on individual EUSR steered A-scans. Using such a hybrid algorithm could result in spatial resolution improvements in both directions—parallel and perpendicular to the direction of propagation of the steered ultrasonic beam.

Figure 15:
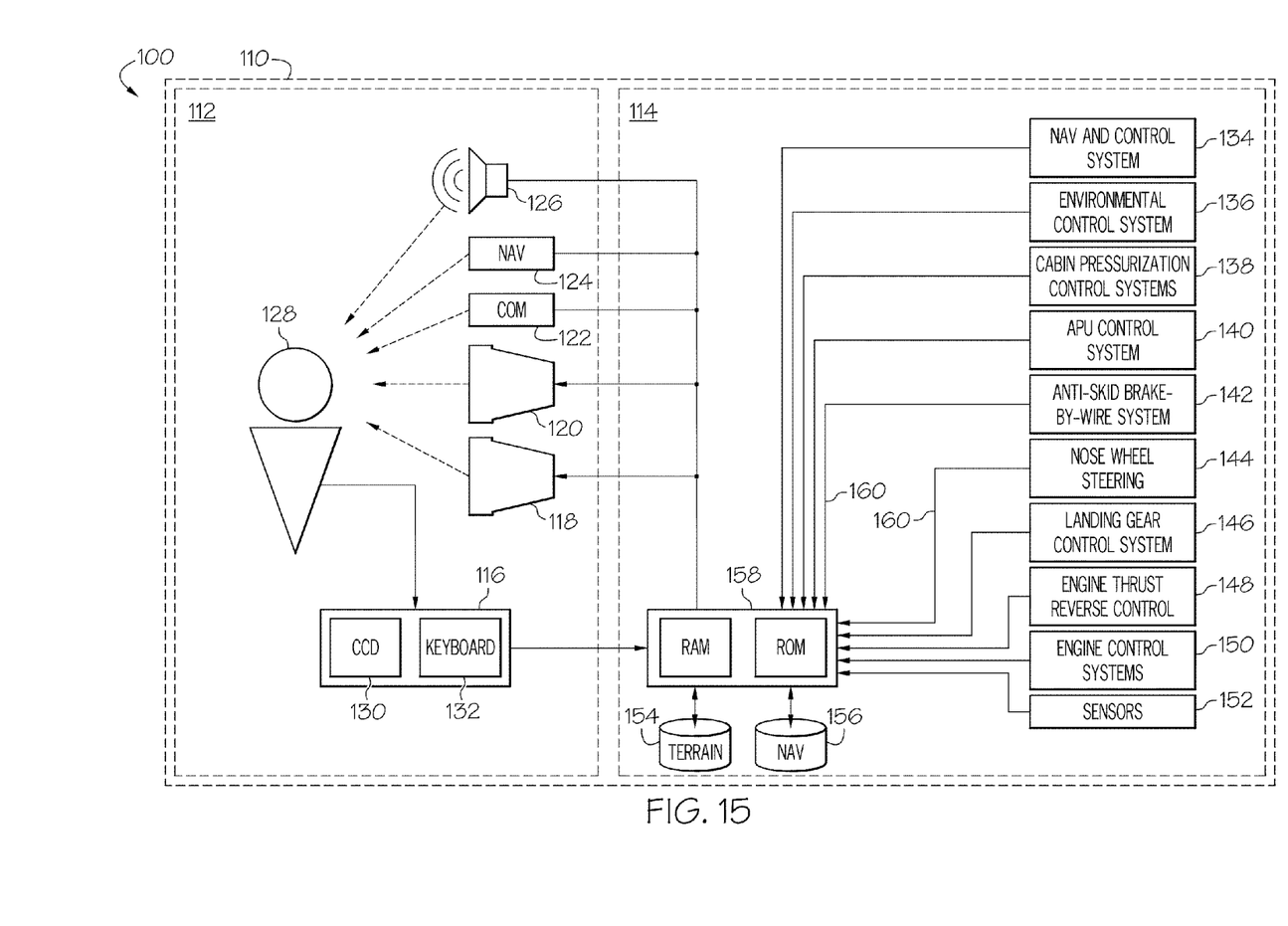
FIG. 15 is a block diagram of a vehicle according to an embodiment.

FIG. 15 schematically illustrates a vehicle 100, such as an aircraft, in which the method and system described above may be implemented, according to one embodiment of the present invention. The vehicle 100 may be, in one embodiment, any one of a number of different types of aircraft such as, for example, a private propeller or jet engine driven airplane, a commercial jet liner, or a helicopter. However, it should be understood that other embodiments may utilize the system described above on vehicles other than aircraft, such as watercraft and land vehicles.

In the depicted embodiment, the aircraft 100 includes a frame (and/or hull) 110, a flight deck 112 (or cockpit) and an avionics/flight system 114. As shown, the flight deck 112 and the avionics/flight system 114 is connected to, or held within, the frame 110. The frame 110 may be made of a metal, such as steel, aluminum, titanium, or a combination thereof. Although not specifically shown in FIG. 15, the sensor assembly (i.e., ultrasonic transducers 18) shown in FIG. 1 may be coupled to the frame 110 of the vehicle and used in the manner described above to detect features (e.g., damage features) within the frame 110.

As shown in FIG. 15, the flight deck 112 includes a user interface 116, display devices 118 and 120 (e.g., a display screen for a flight management system (FMS) and a primary flight display (PFD)), a communications radio 122, a navigational radio 124, and an audio device 126. The user interface 116 is configured to receive manual input from a user 128 (e.g., through a cursor control device 130 and a keyboard 132) and, in response to the user input, supply command signals to the avionics/flight system 114.

The avionics/flight system 114 includes a navigation and control system (or subsystem) 134, an environmental control system (ECS) 136, a cabin pressurization control system (CPCS) 138, an auxiliary power unit (APU) control system 140, an anti-skid brake-by-wire system 142, a nose wheel steering system 144, a landing gear control system 146, an engine thrust reverse control system 148, various other engine control systems 150, a plurality of sensors 152, one or more terrain databases 154, one or more navigation databases 156, and a processor 158. The various components of the avionics/flight system 114 are in operable communication via sensor inputs (e.g., analog sensor inputs) 160 (or a data or avionics bus).

Although not shown in detail, the navigation and control system 134 may include a flight management system (FMS), an inertial navigation system (INS), an autopilot or automated guidance system, multiple flight control surfaces (e.g., ailerons, elevators, and a rudder), an Air Data Computer (ADC), an altimeter, an Air Data System (ADS), a Global Positioning System (GPS) module, an automatic direction finder (ADF), a compass, at least one engine, and gear (i.e., landing gear).

The processor (or processing system) 158 may be any one of numerous known general-purpose microprocessors or an application specific processor that operates in response to program instructions. In the depicted embodiment, the processor 158 includes on-board random access memory (RAM) and on-board read only memory (ROM). The program instructions that control the processor 158 may be stored in either or both the RAM and the ROM (or another computer-readable medium) and may include instructions for carrying out the processes described herein. For example, the operating system software may be stored in the ROM, whereas various operating mode software routines and various operational parameters may be stored in the RAM. It will be appreciated that this is merely exemplary of one scheme for storing operating system software and software routines, and that various other storage schemes may be implemented. It will also be appreciated that the processor may be implemented using various other circuits, not just a programmable processor. For example, digital logic circuits and analog signal processing circuits could also be used.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention.

What is claimed is:

1. A method for detecting features in a thin-wall structure, the method comprising:
    generating a plurality of ultrasonic waves within the thin-wall structure;
    detecting at least one echo from the plurality of ultrasonic waves within the thin-wall structure; and
    processing the at least one echo to determine a position of at least one feature in the thin-wall structure based on Embedded Ultrasonic Structure Radar (EUSR) beamforming performed in the frequency domain, wherein an A-scan for a particular beamsteering angle associated with the EUSR beamforming is defined as $$A(\varphi, t) = \sum_{m=1}^{N} \sum_{n=1}^{N} ifft[X_{mn}(\omega)e^{-i\omega[\delta_m(\omega \cdot d)+\delta_n(\omega \cdot d)]}],$$

where $\phi$ is the beamsteering angle, t is time, m is the transmitting sensor, n is the receiving sensor, $\omega$ is angular frequency, $\delta_m$ is the beamforming delay for the transmitting sensor, $\delta n$ is the beamforming delay for the receiving sensor, and d is a thickness of the thin-wall structure.

2. The method of claim 1, wherein the beamforming delay for the transmitting sensor is defined as $$\delta_m(\varphi, m) = m\frac{D\cos(\varphi)}{c},$$

where D is the spacing between the transmitting sensors and c is the ultrasonic velocity for the material of the thin-wall structure given by Lamb wave dispersion curve for particular Lamb wave mode as a function of the wave frequency—structure thickness product.

3. The method of claim 1, wherein the beamforming delay for the transmitting sensor is defined as $$\delta_m(\vec{r}, \vec{r}_m) = \frac{(r - r_m)}{c},$$

where $\vec{r}$ is the position vector of the target, $\vec{r}_m = \vec{r} - \vec{s}_m$, $\vec{s}_m$ is the position vector of the m$^{-th}$ sensor, and c is the ultrasonic velocity for the material of the thin-wall structure given by Lamb wave dispersion curve for particular Lamb wave mode as a function of the wave frequency—structure thickness product.

4. The method of claim 1, wherein the detecting of the at least one echo is performed with a plurality of sensors coupled to the thin-wall structure.

5. The method of claim 4, wherein the generating of the plurality of ultrasonic waves within the thin-wall structure is performed by the plurality of sensors.

6. The method of claim 5, wherein the plurality of sensors are arranged in a linear array.

7. The method of claim 6, wherein the plurality of sensors comprises piezoelectric actuators.

8. A method for detecting features in a thin-wall structure, the method comprising:

generating a plurality of ultrasonic waves within the thin-wall structure with a plurality of sensors coupled to the thin-wall structure;

detecting at least one echo from the plurality of ultrasonic waves within the thin-wall structure with the plurality of sensors; and processing the at least one echo to determine a position of at least one feature in the thin-wall structure based on Embedded Ultrasonic Structure Radar (EUSR) beamforming performed in the frequency domain, wherein an A-scan for a particular beamsteering angle associated with the EUSR beamforming is defined as $$A(\varphi, t) = \sum_{m=1}^{N} \sum_{n=1}^{N} ifft[X_{mn}(\omega)e^{-i\omega[\delta_m(\omega \cdot d)+\delta_n(\omega \cdot d)]}],$$

where $\phi$ is the beamsteering angle, t is time, m is the transmitting sensor, n is the receiving sensor, $\omega$ is angular frequency, $\delta_m$ is the beamforming delay for the transmitting sensor, $\delta_n$ is the beamforming delay for the receiving sensor, and d is a thickness of the thin-wall structure.

9. The method of claim 8, wherein the beamforming delay for the transmitting sensor is defined as $$\delta_m(\varphi, m) = m\frac{D\cos(\varphi)}{c},$$

where D is the sensor spacing between the transmitting sensors and c is the ultrasonic velocity for the material of the thin-wall structure given by Lamb wave dispersion curve for particular Lamb wave mode as a function of the wave frequency—structure thickness product.

10. The method of claim 8, wherein the beamforming delay for the transmitting sensor is defined as $$\delta_m(\vec{r}, \vec{r}_m) = \frac{(r - r_m)}{c},$$

where $\vec{r}$ is the position vector of the target, $\vec{r}_m = \vec{r} - \vec{s}_m$, $\vec{s}_m$ is the position vector of the m$^{-th}$ sensor, and c is the for the material of the thin-wall structure given by Lamb wave dispersion curve for particular Lamb wave mode as a function of the wave frequency—structure thickness product.

11. The method of claim 8, wherein the plurality of sensors comprises piezoelectric actuators.

12. The method of claim 8, wherein the plurality of sensors are arranged in a linear array.

13. A system for detecting features in a thin-wall structure comprising:

a thin-wall structure;

a plurality of sensors coupled to the thin-wall structure; and a processing system in operable communication with the plurality of sensors, the processing system being configured to:

generate a plurality of ultrasonic waves within the thin-wall structure with the plurality of sensors coupled to the thin-wall structure;

detect at least one echo from the plurality of ultrasonic waves within the thin-wall structure with the plurality of sensors; and determine a position of at least one of the features in the thin-wall structure based on the detected at least one echo, wherein the determining of the position of the at least one of the features is based on Embedded Ultrasonic Structure Radar (EUSR) beamforming performed in the frequency domain, and wherein the processing system is configured such that an A-scan for a particular beamsteering angle associated with the EUSR beamforming is defined as $$A(\varphi, t) = \sum_{m=1}^{N} \sum_{n=1}^{N} i\!f\!f\!t[X_{mn}(\omega)e^{-i\omega[\delta_m(\omega \cdot d)+\delta_n(\omega \cdot d)]}],$$

where $\varphi$ is the beamsteering angle, t is time, m is the transmitting sensor, n is the receiving sensor, $\omega$ is angular frequency, $\delta_m$ is the beamforming delay for the transmitting sensor $\delta_n$ is the beamforming delay for the receiving sensor and d is a thickness of the thin-wall structure.

14. The system of claim 13, wherein the processing system is configured such that the beamforming delay for the transmitting sensor is defined as $$\delta_m(\varphi, m) = m\frac{D\cos(\varphi)}{c},$$

where D is the sensor spacing and c is the ultrasonic velocity for the material of the thin-wall structure given by Lamb wave dispersion curve for particular Lamb wave mode as a function of the wave frequency—structure thickness product.

15. The system of claim 13, wherein the processing system is configured such that the beamforming delay for the transmitting sensor is defined as $$\delta_m(\vec{r}, \vec{r}_m) = \frac{(r - r_m)}{c},$$

where $\vec{r}$ is the position vector of the target, $\vec{r}_m = \vec{r} - \vec{s}_m$, $\vec{s}_m$ is the position vector of the $m^{-th}$ sensor, and c is the ultrasonic velocity for the material of the thin-wall structure given by Lamb wave dispersion curve for particular Lamb wave mode as a function of the wave frequency—structure thickness product.

16. The system of claim 13, wherein the plurality of sensors comprises piezoelectric actuators.

17. The system of claim 13, wherein the thin wall structure is a portion of a vehicle.

* * * * *